United States Patent
Perrier et al.

(10) Patent No.: US 8,408,042 B2
(45) Date of Patent: Apr. 2, 2013

(54) DEVICE FOR GENERATING IMPACTS WITH A STRUCTURE

(75) Inventors: Aurelien Perrier, Bagneux (FR); Gilbert Le Floc'h, Parempuyre (FR)

(73) Assignee: Astrium SAS, Paris (FR)

( * ) Notice: Subject to any disclaimer, the term of this patent is extended or adjusted under 35 U.S.C. 154(b) by 627 days.

(21) Appl. No.: 12/307,938

(22) PCT Filed: Jul. 10, 2007

(86) PCT No.: PCT/EP2007/057017
§ 371 (c)(1),
(2), (4) Date: Oct. 6, 2009

(87) PCT Pub. No.: WO2008/006822
PCT Pub. Date: Jan. 17, 2008

(65) Prior Publication Data
US 2011/0132069 A1      Jun. 9, 2011

(30) Foreign Application Priority Data
Jul. 10, 2006 (FR) .................................. 06 52888

(51) Int. Cl.
G01M 7/00 (2006.01)
G01N 3/00 (2006.01)
G01N 33/00 (2006.01)
G01P 15/00 (2006.01)

(52) U.S. Cl. ....................... 73/12.11; 73/12.09; 73/12.01
(58) Field of Classification Search ................. 73/12.01, 73/12.09, 12.11
See application file for complete search history.

(56) References Cited

U.S. PATENT DOCUMENTS

| 5,184,499 A | | 2/1993 | Oppliger et al. | |
| 5,497,649 A | * | 3/1996 | Ambur et al. ................ | 73/12.06 |
| 5,739,411 A | * | 4/1998 | Lee et al. ..................... | 73/12.13 |
| 6,257,352 B1 | * | 7/2001 | Nelson .......................... | 173/211 |
| 2005/0188744 A1 | | 9/2005 | Cambio | |

FOREIGN PATENT DOCUMENTS

| DE | 31 28 711 A1 | 2/1983 |
| DE | 100 09 987 A1 | 9/2001 |
| EP | 1 553 393 A | 7/2005 |
| GB | 2 379 276 A | 3/2003 |

OTHER PUBLICATIONS

Author: Samuel Ibekwe, Ph.D.,Title: "DURIP-97 Enhancement of DOD Related Research Through Acquisition of Impact Testing Equipment", Date: Mar. 31, 1998, pp. 1-27.*

* cited by examiner

Primary Examiner — Lisa Caputo
Assistant Examiner — Roger Hernandez-Prewitt
(74) Attorney, Agent, or Firm — Perman & Green, LLP

(57) ABSTRACT

A device for generating impacts on a structure has a projectile head. The head includes a main body on which an impact element is mounted so it projects. The device includes a mechanical propulsion element to set the projectile head in motion, and the propulsion element can move between an initial resting position where the propulsion element is immobile and the projectile head is held against the propulsion element by at least one retaining element, and a second position where after the propulsion element comes to a stop against stop elements, the projectile head moves alone in translation toward the structure guided by guidance elements. The device also includes an anti-rebound system to prevent any rebound by the projectile head after impact on the structure.

12 Claims, 2 Drawing Sheets

DEVICE FOR GENERATING IMPACTS WITH A STRUCTURE

CROSS-REFERENCE TO RELATED APPLICATIONS

This application is the National Stage of International Application No. PCT/EP2007/057017, international Filing Date, Jul. 10, 2007, which designated the United States of America, and which International Application was published under PCT Article 21(s) as WO publication No. WO 2008/006822 A1 and which claims priority from, and the benefit of, French Application No. 0652888 filed on Jul. 10, 2006.

This invention concerns a device for generating impact on a structure, notably low energy for purposes of control.

BACKGROUND

Structures made of composite materials are being used more and more often in industry, particularly in cutting-edge industries, such as aeronautics and aerospace, but also in the manufacture of series components for automobiles, boats and trains.

These materials have excellent mechanical, static and dynamic properties and low density.

However, structures made of these materials are particularly sensitive to direct shock or impact, which can cause damage or even perforation. These kinds of shock can therefore substantially alter the mechanical characteristics of these structures and prevent them from performing their functions.

To date, composite materials have been used mainly for non-structural parts, like aerodynamic hoods or for structural parts located in "protected" areas, since these parts are not very capable of withstanding environmental hazards.

But today, there are attempts to use these composite materials to build aircraft fuselages or wings or train trucks . . . to improve the performance of these means of transportation. These composite materials will therefore be particularly exposed to direct shocks.

It therefore makes sense to study the risks associated with the mechanical shocks that such parts could suffer to ascertain their behavior and determine whether they can still function nominally despite the presence of one or more impacts.

SUMMARY

The object of the invention is a machine that makes it possible to generate direct and representative shocks on a component on a real scale. The shock can then be located anywhere on the component, for example on top or on the sides.

More specifically, the invention involves generating so-called "low-energy" shocks, which are the little shocks of daily life, like those caused by a tool falling: the velocities are then on the order of several meters per second.

A machine that makes it possible to generate shocks on mechanical components is known from US patent application 2005/0188744.

This machine has an impactor and a pneumatic energy source with a pneumatic cylinder to set the impactor in motion. The impactor has a laser measurement head, an anti-rebound system composed of a simple return spring and a residual energy absorber.

However, this machine has several disadvantages.

Since the energy source is pneumatic, it is necessary to make sure that the moving parts are sealed. There is consequently friction and, hence, energy consumption by the impactor that is not known in its so-called "ballistic" phase.

Such an installation is also very complex and can pose problems with test reliability and especially reproducibility.

The system for measuring the energy of the shock is comprised of an onboard laser. Now, it is well known that the precision of laser speed measurement is not very good, and several measurements must be averaged to obtain a significant measurement.

It is also unsatisfactory to load a measurement system on a component subject to shock, and this measurement system cannot determine the rebound energy. This makes it hard to determine the forces on impact. Finally, there are health risks to the operators that are associated with the presence of the laser beam.

The anti-rebound system is, as indicated above, comprised of a simple return spring. By definition, such a spring is a consumer of the ballistic energy transmitted to the impactor. This energy consumption is dependent on the course of the impactor, so it is very complex to set the test parameters.

Finally, the machine described has no frame, which implies an extremely complex and pneumatic safety system subject to potential human error. There is therefore no certainty of operator safety.

The goal of this invention is therefore to propose a device for generating impact on a structure that is simple in design and operating mode, particularly reliable and safe and makes it possible to generate impacts over a broad range of forces. These impacts can also be applied at any angle of incidence.

Another object of this invention is such a device equipped with sensors connected to a processing unit that make it possible to determine the velocity and the force as a function of the time of the impact head and to know the forces at the moment of shock of said head and of the structure to understand the mechanisms and the consequences of the damage to the composite materials, knowledge of which is still very incomplete.

To this effect, the invention concerns a device for generating impact on a structure that includes a projectile head.

According to the invention, said head has a main body on which a projecting impact element is mounted, said device includes a mechanical propulsion element to set the projectile head in motion, the mechanical propulsion element can move between a first, so-called resting position where this mechanical propulsion element is immobile and the projectile head is held against it by at least one retaining element, and a second position where this mechanical propulsion element strikes stop elements and the projectile head moves in translation toward the structure guided by guidance elements, the device also has an anti-rebound system to prevent the projectile head from rebounding after impact on the structure.

The impact-generating device has the advantage of being made to form an integrated whole, in the sense that the projectile head cannot be mechanically detached from the frame of the device. It is therefore not dangerous to the operators. The device also uses mechanical energy to set the projectile element in motion that is determined exactly and can easily be incremented by a pitch of known value. Finally, the measuring instruments are placed in a non-mobile area of the device.

These measuring instruments are used advantageously not only to control the test conditions, but also to help interpret the results obtained.

In different special embodiments of this impact-generating device, each having its special advantages and capable of many possible technical combinations:

- the mechanical propulsion element has at least two compression springs, and the device has a mechanism to place these springs under tension,
- the anti-rebound system includes at least two jacks supporting the main body of the projectile head on either side of the impact element,
- these jacks are pneumatic jacks,
- the device has at least one displacement transducer, Preferably, this sensor is a capacitive displacement transducer,
- the device is able to project the projectile head onto the structure with an impact force less than or equal to 200 joules±2.5%,
- the velocity v of the projectile head is less than or equal to 5 m.s$^{-1}$.

BRIEF DESCRIPTION OF THE DRAWINGS

The invention will be described in greater detail with reference to the attached drawings in which.

DETAILED DESCRIPTION

Figure 1:
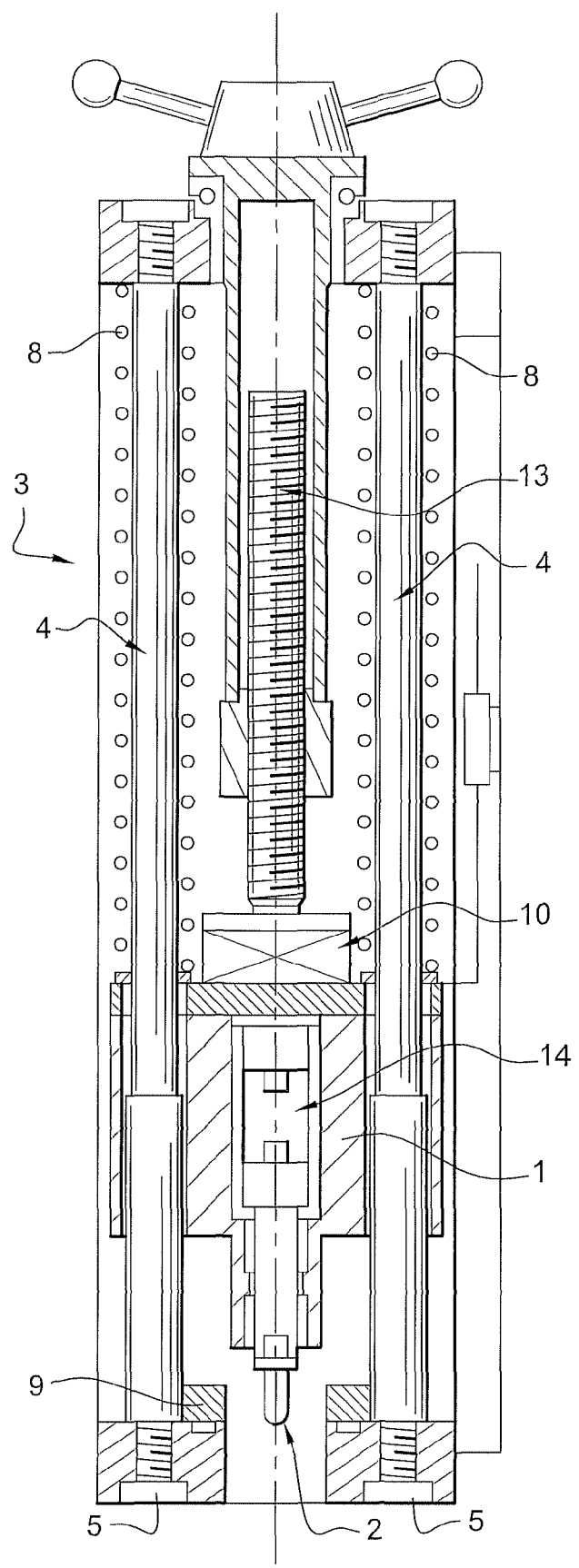
FIG. 1 is a schematic view of a device for generating impact on a structure before the projectile head is launched, according to one special embodiment of the invention.
Figure 2:
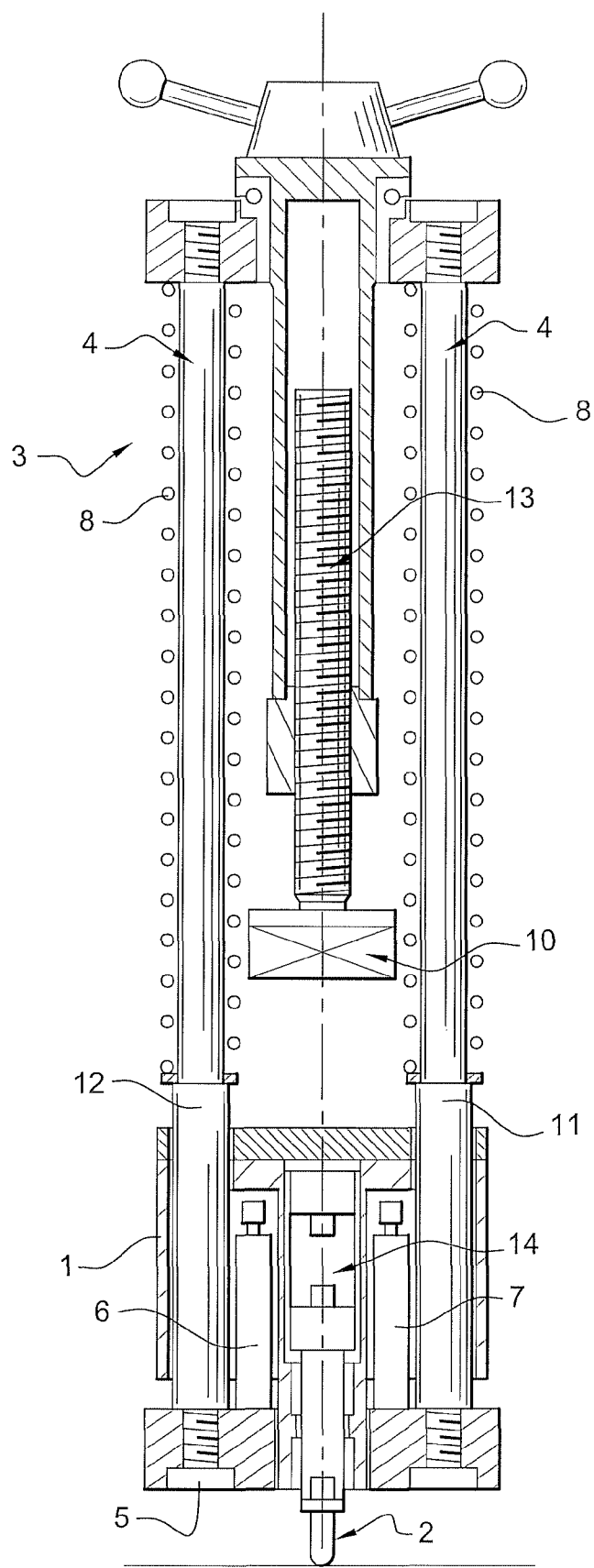
FIG. 2 is a schematic view of the device in FIG. 1 after the projectile head is launched.

FIG. 1 shows a device for generating impact on a structure according to one special embodiment of the invention. This device includes a projectile head having a main body 1 on which an impact element 2 is mounted so it projects and can be removed. This impact element 2 is thus interchangeable and can have a shape chosen from the group that includes a hemispherical shape, a cylindrical shape, a conical shape or another.

The diameter of this impact element 2 is typically between several millimeters and several tens of millimeters. It is preferably metallic, but can also be made of hard plastic or something else based on the impact simulation to be carried out.

To simulate low-energy shocks, the impact force or pressure force expressed in joules applied to the structure will typically be less than or equal to 200 joules. The speed of the projectile head will be less than 5 m/s to adequately represent a low-energy shock.

Low-impact energies are obtained either by reducing the constant mass velocity of the projectile head, which is one preferred approach, by reducing the mass of the projectile head to a constant impact velocity, or by varying the two simultaneously.

In the case where the mass of the projectile head is varied, the main body 1 of the projectile head can have points of attachment for additional loads that make it possible to change the mass of this projectile head with its impact element.

The device has a frame 3 with guidance elements 4 mounted on bases 5, and these guidance elements 4 define a free zone for the passage of the impact element 2. An anti-rebound system 6, 7 is placed between the free zone and the guidance elements 4 on the lower part of the frame 3, while the frame is connected to a mechanical propulsion element 8 on its upper part.

These guidance elements 4 are columns along which the projectile head can move. The bases 5 preferably have safety stops 9, for example made of rubber, whose role is to limit the course of the impact element 2 in the event that the device malfunctions without damaging it and without the malfunctions being able to constitute a danger to the operators. The base/columns unit thus forms the mechanical limits of the device.

The mechanical propulsion element 8 makes it possible to set the projectile head in motion. It can move between an initial so-called resting position where this mechanical propulsion element 8 is immobile and is located on the upper part of the frame 3, with the projectile head held against it by a retaining element 10, and a second position where this mechanical propulsion element 8 comes to a stop against stop elements 11, 12 and the projectile head moves in translation toward the structure guided by the guidance elements 4.

Before the test, the projectile head is thus held in position by the retaining element 10, which is preferably an electromagnet. An "axial" or "finger"-type mechanical system can be used to make sure this attachment is secure. Double electric security is also provided by an autonomous backup battery. This backup battery is placed on an auxiliary circuit that makes it possible to power the retaining element 10 in the event that its main power source fails. This retaining element 10 is advantageously powered by the mains.

An offsite control box (not shown) allows the operator to activate or deactivate the retaining element 10 to launch the projectile head with its impact element or not.

The mechanical propulsion element 8 preferably has two compression springs tightened with a screw 13.

Since these springs have a mobile extremity along the guidance elements 4, the stop elements 11, 12 are comprised of a shoulder placed on each column 4. These shoulders 11, 12 are capable of stopping the movement of the compression springs, with the projectile head then moving alone toward the structure until the impact element comes in contact with the latter.

The anti-rebound system 6, 7 prevents any rebound by the projectile head after the impact element 2 hits the structure. This anti-rebound system preferably has two pneumatic jacks 6, 7 supporting the main body 1 of the projectile head on either side of the impact element 2. These jacks 6, 7 are triggered by a sensor such as a photoelectric cell that detects the passage of the projectile head near said safety stops 9, when ascending or descending, depending on the test. It is possible to adjust the triggering of the anti-rebound system optionally to make the projectile head go and return. Triggering the go is an advantage that makes it possible to compensate for the inertia of the anti-rebound system. Prior refinement may be necessary, depending on the structure to be impacted. Indeed, the stiffer the structure and the faster the projectile head rebounds, the sooner it will be necessary to trigger the anti-rebound system. The device includes a compressed air power source connected to said anti-rebound jacks 6, 7.

To measure the displacement of the projectile head before and after impact on the structure, the device includes a capacitive displacement transducer (not shown). This transducer makes it possible to access by derivation the velocity and the force as a function of the time and the impact head.

A force sensor with strain gages 14 makes it possible to know the force at the time of the shock. These sensors are preferably connected to a central processing unit that makes it possible to store and process the data received.

A telescopic arm can be used to move and orient the device in relation to the structure being impacted. It thus makes it possible to determine the angle of impact of the impact element.

To use this device, the data to be taken into account are:
the force of the impact,
the type of impact element used,
the position of the impact to be applied,
the direction of the impact to be applied in relation to the vertical, and
potentially the velocity of the impact element.

The use of the device also requires prior calibration that makes it possible to know the impact force as a function of the direction of the impact in relation to the vertical, on one hand, and the initial force of the projectile head, on the other, namely its kinetic energy, as provided by the springs. This prior calibration makes it possible to know with precision the stiffness of the springs 8 used to propel the projectile head. Of course, this calibration occurs only in the initial validation phase of the device.

The test conditions and the calibration of the device make it possible to determine the compression to be applied to the springs to obtain a certain impact force and vary it with a pitch, which may be 1 joule.

After the device is positioned on the structure to be impacted, the safety axis is removed, and the test is started by deactivating the retaining element 10. The mechanical propulsion element 8 propels the projectile head, which continues its course due to inertia when the mechanical propulsion element 8 is stopped by the stop elements 11, 12.

The capacitive displacement transducer makes it possible to measure the displacement of the projectile head during its inertial displacement before and after impact. Deriving the signal makes it possible to find the velocity of the projectile head and hence the force before and after impact.

It is thus possible to obtain the force absorbed for the structure, as well as the material characteristics at the time of the shock using the sensor with strain gages 14.

Finally, the anti-rebound system 6, 7 detects that the impact has occurred, and prevents the projectile head from rebounding on the structure again to make sure that the projectile head only hits the structure being tested once. As explained above, the projectile head does, however, rebound on the impacted structure.

This device can be used in any field of industry where structural composites are used: transportation, but also by the petroleum industry, for example.

The invention claimed is:

1. A device for generating impacts on a structure, with said device comprised of a projectile head, wherein
said head has a main body on which an impact element is mounted so it projects,
the device has a mechanical propulsion element to set said projectile head in motion,
said mechanical propulsion element can move between:
an initial resting position where said mechanical propulsion element is immobile and said projectile head is held against the propulsion element by at least one retaining element, and
a second position where after said mechanical propulsion element comes to a stop against stop elements, said projectile head moves alone in translation toward said structure being guided by guidance elements,
wherein said device also includes an anti-rebound system to prevent any new rebound by said projectile head after impact on said structure, and
wherein said retaining element is an electromagnet.

2. The device of claim 1, comprising a frame with said guidance elements mounted on bases; wherein said guidance elements define a free zone for the passage of said impact element; said anti-rebound system is placed between said free zone and said guidance elements on the bottom part of said frame and said mechanical propulsion element is connected to said frame on a top part.

3. The device of claim 1, wherein said guidance elements are columns.

4. The device of claim 1, wherein said mechanical propulsion element has at least two compression springs, and the device has a mechanism to place said springs under tension.

5. The device of claim 4, wherein said springs have a mobile extremity along said guidance elements, and said stop elements are comprised of a shoulder placed on each column.

6. The device of claim 1, wherein said anti-rebound system has at least two jacks supporting the main body of said head on either side of the impact element.

7. The device of claim 6, wherein said jacks are pneumatic jacks.

8. The device of claim 1, comprising at least one displacement transducer.

9. The device of claim 8, comprising a force sensor with strain gages.

10. The device of claim 1, wherein said impact element is removably mounted on said main body.

11. The device of claim 1, wherein said impact element has a shape chosen from the group that includes hemispheric, cylindrical and conical shapes.

12. The device of claim 1, wherein a velocity v of said projectile head is less than or equal to 5 m.s-1.

* * * * *